United States Patent

Ono et al.

[11] Patent Number: 5,938,931
[45] Date of Patent: Aug. 17, 1999

[54] METHOD FOR PROCESSING LIQUID CHROMATOGRAPHIC DATA

[75] Inventors: Takayuki Ono; Masahiro Taki, both of Hitachinaka, Japan

[73] Assignee: Hitachi, Ltd., Tokyo, Japan

[21] Appl. No.: 08/958,919

[22] Filed: Oct. 28, 1997

[30]     Foreign Application Priority Data

Oct. 31, 1996  [JP]  Japan .................................. 8-290230

[51] Int. Cl.⁶ ................................................. B01D 15/08
[52] U.S. Cl. ..................... 210/656; 210/198.2; 73/61.52; 703/23; 703/30; 703/32; 436/161
[58] Field of Search .................................. 210/656, 659, 210/96.1, 101, 198.2; 422/70; 436/161; 703/23, 30, 32; 73/61.52

[56]            References Cited

U.S. PATENT DOCUMENTS

| | | | |
|---|---|---|---|
| 4,468,742 | 8/1984 | Jenden | 364/497 |
| 4,719,017 | 1/1988 | Uchino | 210/656 |
| 5,039,409 | 8/1991 | Blaffert | 210/198.2 |
| 5,203,992 | 4/1993 | Drouen | 210/198.2 |
| 5,668,735 | 9/1997 | Dominguez | 702/31 |

*Primary Examiner*—Ernest G. Therkorn
*Attorney, Agent, or Firm*—Kenyon & Kenyon

[57]            ABSTRACT

A data processing method in a liquid chromatograph provided with a column, a device for pouring an eluting solution into the column to elute respective samples injected into the column to thereby separate components of the samples, a data processor for detecting and data processing the separated components to thereby obtain analysis results constituted by chromatograms and quantitative calculation results of the respective samples, and a display unit for displaying the analysis results. The method comprises the steps of: storing the analysis results of the respective samples in a memory in the data processor with correspondence between the analysis results and the respective samples; displaying, on the display unit, a sample information table expressing injection data concerning the samples injected; reading the analysis results of a specific sample from the memory when the specific sample is designated from the sample information table; and displaying the read analysis results as a print preview on the display unit.

4 Claims, 6 Drawing Sheets

CALIBRATION CURVE 1

CALIBRATION CURVE 2

FIG. 7

ANALYSIS RESULT PORTION

ANALYSIS REPORT

PEAK QUANTIFICATION : AREA
QUANTITATIVE CALCULATION METHOD
  : ABSOLUTE CALIBRATION CURVE METHOD
FACTOR 1 : 1,000

| NO | RT | AREA | COMPONENTS | DENSITY 1 (ppm) |
|----|------|--------|------------|-----------------|
| 1  | 2.33 | 150837 | Naphthal   | 10              |
| 2  | 2.64 | 228967 | Authrace   | 0.3             |
| 3  | 3.10 | 58000  | Chrysene   | 0.375           |
|    |      | 437804 |            | 10.675          |

JUDGMENT LEVEL OF REPORTED PEAK : 0

| VIAL NO. | INJECTION QUANTITY | INJECTION NUMBER OF TIMES | SAMPLE NAME | SAMPLE COMMENT |
|----------|--------------------|---------------------------|-------------|----------------|
| 1 | 0  | 1 | BLANK1    | |
| 2 | 2  | 1 | STANDARD2 | |
| 3 | 4  | 1 | STANDARD3 | |
| 4 | 6  | 1 | STANDARD4 | |
| 5 | 8  | 1 | STANDARD5 | |
| 6 | 10 | 1 | UNK1      | |
| 7 | 10 | 1 | UNK2      | |
| 8 | 10 | 1 | UNK3      | |
| 9 | 10 | 1 | UNK4      | |

SAMPLE INFORMATION TABLE PORTION

METHOD FOR PROCESSING LIQUID CHROMATOGRAPHIC DATA

BACKGROUND OF THE INVENTION

The present invention relates to a liquid chromatograph, and particularly to a method for processing data of liquid chromatograph, which has a function of print-previewing analysis results.

In a liquid chromatograph, after collection of chromatographic data and before printing of analysis results, an analyst makes a judgement, by watching a print preview screen, as to whether analysis results are obtained as expected or not. In accordance with the judgment, quantitative calculation for obtaining analysis results may be repeated several times upon chromatographic data once collected. In order to watch the analysis results of an unknown sample whenever quantitative calculation is executed, the page of the analysis results of the unknown sample must be searched for while pages are turned over one by one after the first page generally indicating the analysis results of a known standard sample is displayed by print previewing.

In the print preview, unless the page of the analysis results of an unknown sample is displayed with one-to-one correspondence with a sample (analyte) information table in which the quantities of injected standard samples and unknown samples, the names of the samples and the vial numbers of the samples (the positions of the samples arranged on the sample table) are arranged correspondingly to the respective injected samples, the analyst cannot directly watch the analysis results corresponding to the unknown sample requested by the analyst.

SUMMARY OF THE INVENTION

An object of the present invention is to provide a method for liquid chromatographic data suitable for performing print previewing of analysis results directly and speedily for every sample on a sample information table.

In order to achieve the above object, the liquid chromatograph according to the present invention comprises a column, a device for pouring an eluting solution into the column to elute respective samples injected into the column to thereby separate components of the samples, a data processor for detecting and data processing the separated components to thereby obtain analysis results of the respective samples, and a display unit for displaying the analysis results, the data processor including a memory for storing the analysis results of the respective samples with correspondence between the analysis results and the respective samples, so that a sample information table expressing injection data concerning the injected samples is displayed on the display unit and, when a sample in the table is designated, the analysis results of the designated sample is read from the memory so as to be displayed on the display unit for print previewing.

A schematic procedure from the point of time when an analyst sets data processing conditions to the point of time when print previewing of analysis results is carried out to display analysis results of an unknown sample will be described below.

First, a user determines a system configuration (a device configuration which is inputted through a data processor) for defining various devices of a chromatographic unit constituting a system, device conditions (such as the flow rate and pressure of a pump, the inflow of a sampler, etc.) for the respective devices of the chromatographic unit, and data processing conditions (equations for quantitative analysis calculation).

This system configuration, the device conditions for the respective devices of the chromatographic unit and the data processing conditions are stored in a memory of the data processor.

When the analyst starts a measurement, the data processor which serves also as a controller for the respective devices of the chromatographic unit performs analysis in accordance with the aforementioned three analysis conditions stored in the memory. After the completion of the analysis, the data processor reads the data processing conditions set in advance by the analyst from the memory and performs data processing on each of the measured analytes. The results of data processing are stored as analysis results in the memory included in the data processor.

Generally, the analyst does not immediately supply the analysis results to a printer but confirms the results of data processing on an unknown sample by print previewing. When print previewing is executed, not only the first page of the analysis results is displayed but also information of respective samples (analytes) subjected to data processing is displayed, that is, a sample (analyte) information table on which the quantities of injected samples, the names of the samples and the vial numbers of the samples are arranged in the order of injection of the samples is displayed.

The analyst designates an analyte of a specific unknown sample from the sample information table, and makes the page of the analysis results of the unknown sample be displayed again to confirm the content of the page.

As described above, because the analysis results of a requested analyte can be displayed directly by using an analyte information table, a requested page can be displayed without necessity of searching for analysis results of unknown samples while turning over the pages of the analysis results, unlike the prior art.

BRIEF DESCRIPTION OF THE DRAWINGS

FIG. 7 is a graph showing an example of a screen calculated on the basis of the calibration curve depicted in FIG. 6.

DESCRIPTION OF THE PREFERRED EMBODIMENTS

An embodiment of the present invention will be described below with reference to the drawings.

Figure 3:
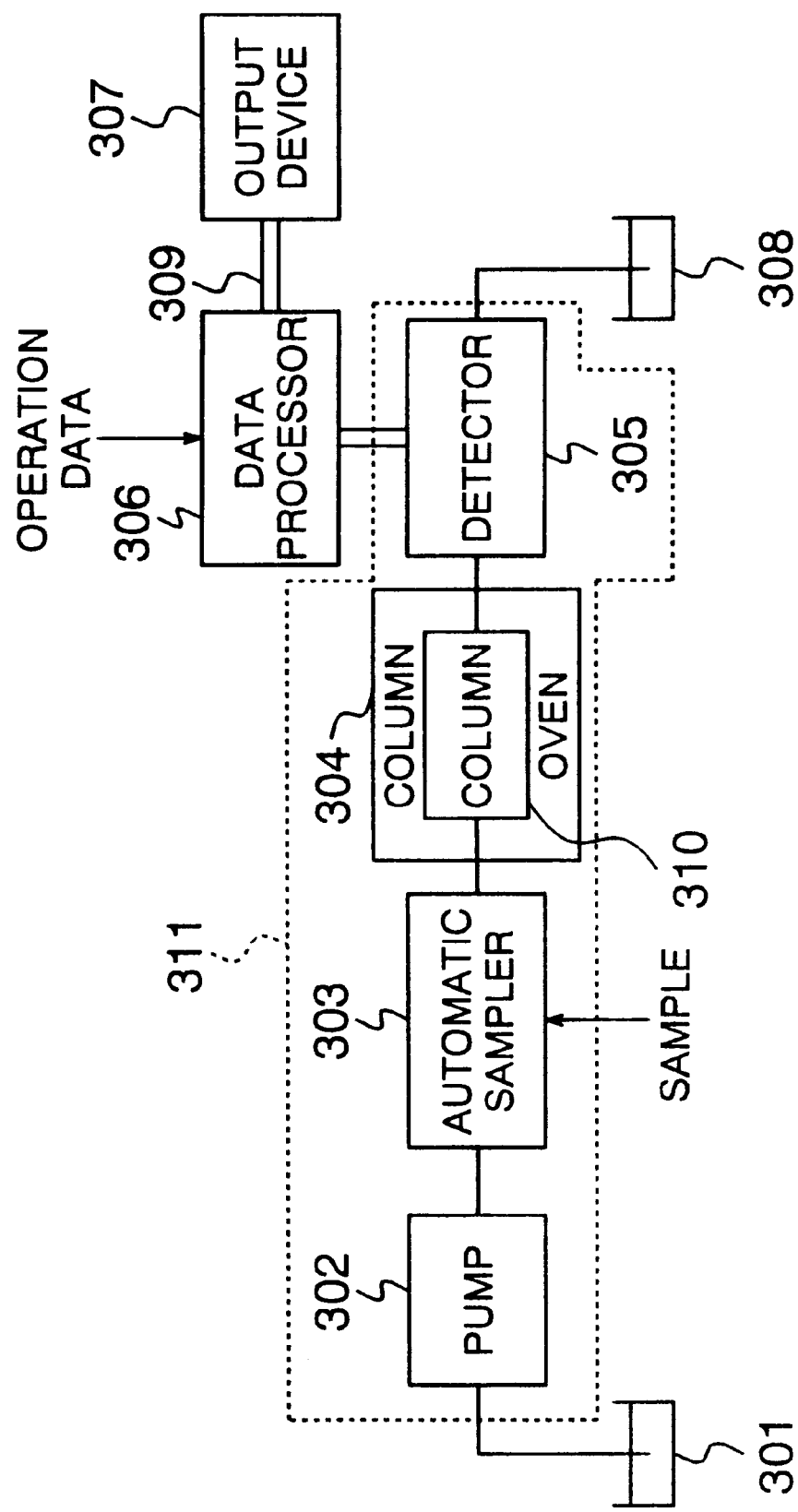
FIG. 3 is a system configuration view of the liquid chromatograph in this embodiment.

Referring now to FIG. 3, the configuration and theory of a liquid chromatograph will be described. In a liquid chromatograph unit 111, the reference numeral 301 designates an eluting solution tank; 302, a pump; 303, an automatic sampler; 304, a column oven; and 305; a detector. The reference numeral 306 designates a data processor including a memory for controlling the various devices 302 to 305 of the chromatographic unit 311. The reference numeral 307 designates an output device including a display unit, and a printer. The reference numeral 309 designates a communication line. A sample injected by means of the automatic sampler 303 is fed, by means of the pump 302, together with an eluting solution to a column 310 in the column oven 304. The column 310 is kept thermostatic in the column oven 404. In this condition, the sample is eluted, so that the components of the sample are separated and detected by the detector 305. The components thus detected are subjected to data processing by the data processor 306, so that the analysis results of the sample as the thus obtained data are supplied to the output device 307 and indicated on the display unit included in the output device 307. Incidentally, the reference numeral 308 designates a waste solution tank.

Figure 1:
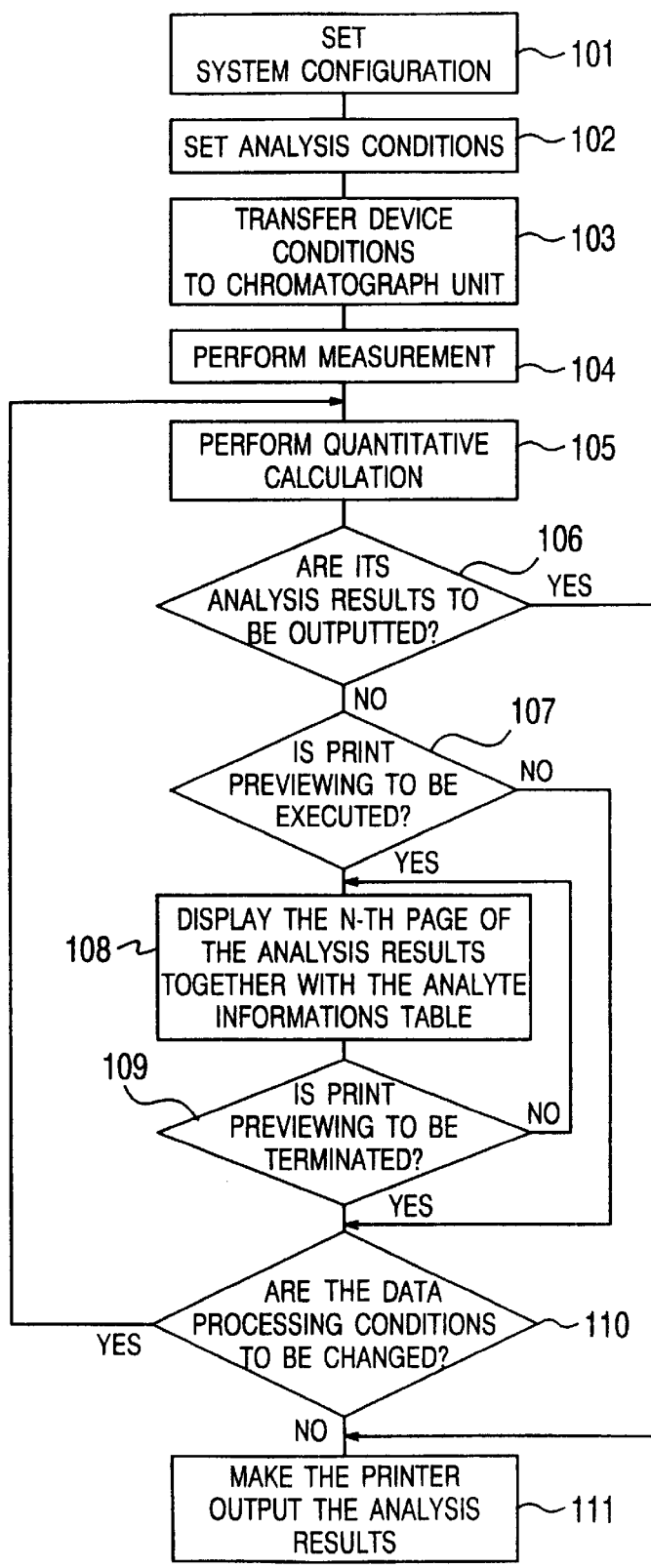
FIG. 1 is a flow chart for explaining an example of a data processor portion in a liquid chromatograph as an embodiment of the present invention.
Figure 2:
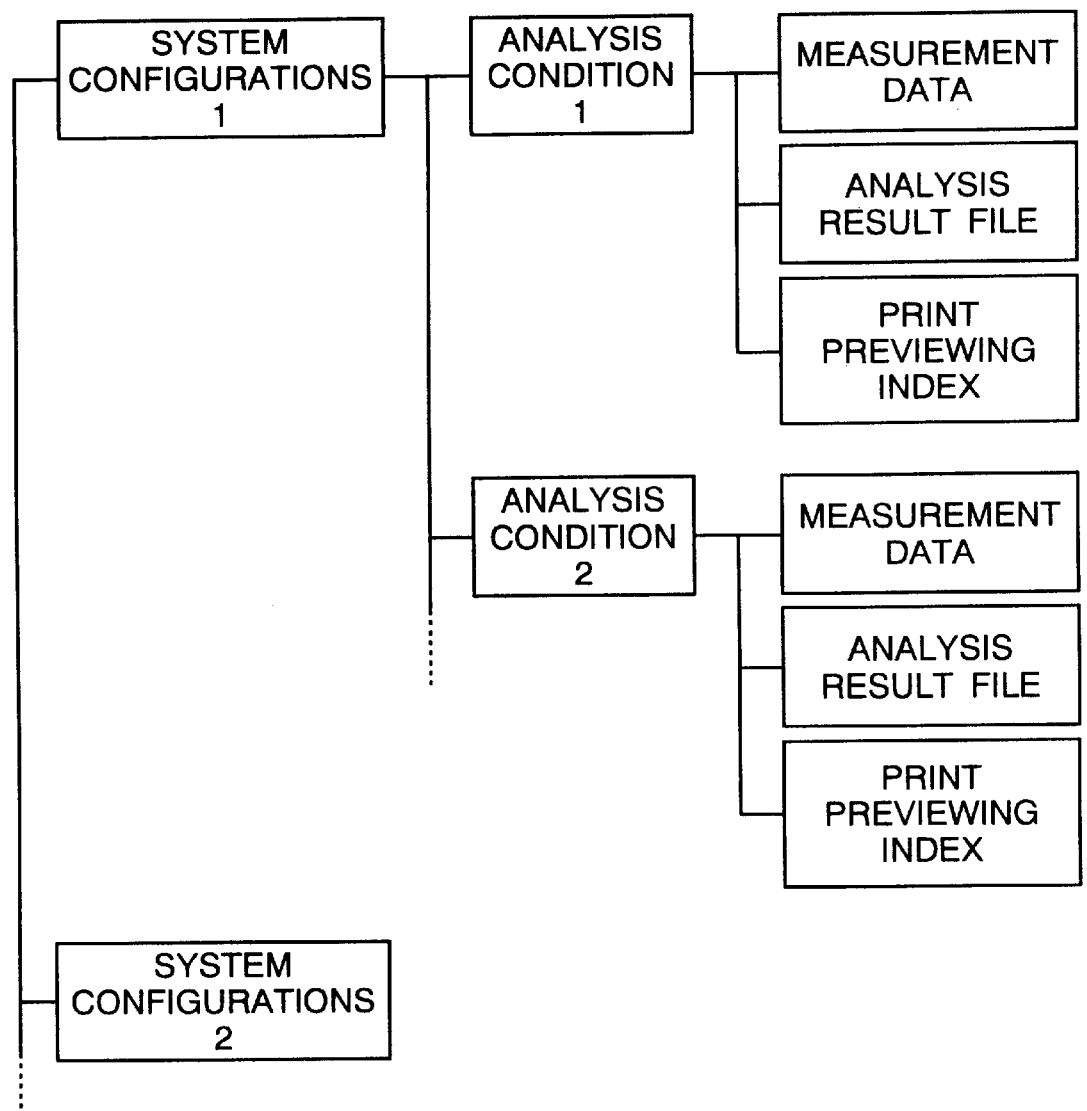
FIG. 2 is a view showing the configuration of a file as an example of data stored in a memory included in the data processor portion in the liquid chromatograph in this embodiment.

Referring next to FIGS. 1 and 2, an example of the processing according to the present invention will be described.

Step 101: At the start of analysis, the analyst first inputs, into the data processor 306 a system configuration file for designating the contents of various devices of the chromatographic unit 311 constituting the liquid chromatograph to thereby generate the system configuration file. As described above and as shown in FIG. 3, the devices of the chromatographic unit 311 constituting the liquid chromatograph are the pump 302, the automatic sampler 303, the column oven 304 and the detector 305.

Step 102: Analysis conditions, that is, the device conditions of the respective devices of the chromatographic unit 311 and the data processing conditions are supplied into the data processor 306 so as to be stored therein. For examples, the device conditions of the respective devices of the chromatographic unit 311 may include the quantities of samples injected into the automatic sampler 303, the number of times of injection, the eluting solution mixture proportion and the upper and lower limits of the flow rate and pressure of the pump 302, the setting value of the temperature of the column oven 304, the measurement wavelength and measurement time of the detector 305, and so on. The device conditions of the respective devices of the chromatographic unit and data processing conditions generated by the analyst are stored under a directory of the system configuration generated in the step 101.

Referring to FIG. 2, description will be made specifically. In a memory of the data processor 306, there is provided an area for storing the analysis conditions generated by the analyst, measurement data as crude data, analysis result files and print previewing indexes for previewing, so that the device conditions of the respective devices of the chromatographic unit 311 and data processing conditions generated by the analyst are stored in this area. The device conditions of the respective devices of the chromatographic unit 311 and data processing conditions generated by the analyst are stored for every system configuration corresponding thereto. That is, when the system configuration generated by the analyst is identical to "system configuration 1" as shown in FIG. 2, the analysis conditions are stored in a directory of "analysis condition n" having the largest management number in the directories under the "system configuration 1".

When the system configuration is different from any of existing system configurations, a directory of "system configuration m" having the largest management number is generated newly and respective data are stored in this directory.

Step 103: The device conditions generated in the step 102 for the respective devices of the chromatographic unit 311 are transferred from the data processor 306 to various devices of the chromatographic unit 311 via the communication line 309.

Step 104: After the device conditions are transferred to the respective devices of the chromatographic unit 311, the analyst makes the data processor 306 execute measurement so that the data processor 306 requests the various devices of the chromatographic unit constituting the liquid chromatograph to perform measuring operations. The chromatographic data as the results of analysis in accordance with the device conditions are transferred to the data processor after the completion of the measurement. The measurement data thus transferred are temporarily stored in the measurement data storage area of the data processor.

Step 105: Upon reception of the chromatographic data, the data processor 306 executes quantitative calculation in accordance with the data processing conditions stored in the data processor 306. After the completion of the quantitative calculation, a new page is opened for every sample and the calculation results are outputted to the analysis result file.

In this occasion, a printing previewing index in which correspondence between each sample and a leading page of the analysis results of the sample are generated. As shown in FIG. 2, the print previewing index thus generated is stored, together with the measurement data and the analysis result file, in the memory included in the data processor 306.

Step 106: When the analyst judges that it is not necessary for the analyst to confirm the analysis results by print previewing, the data processor 306 executes printing of the analysis results without carrying out the confirmation by means of print previewing (step 111).

Step 107: When the analyst wishes to confirm the contents of the analysis results, print previewing is executed before the analysis results are printed as reports in the step 105.

Step 108: When print previewing is executed, the analysis results are read from the analysis result file and the leading page concerning BLANK1 of vial No. 1 is displayed. At the same time as the analysis results are displayed, sample information, that is, a sample information table on which the quantities of injected samples, the names of the samples and the vial numbers of the samples are arranged correspondingly to the respective injected samples is also displayed as shown in FIG. 4.

The analyst designates a sample the content of which the analyst wishes to confirm from the sample information table. In response to the designation, the data processor searches the print previewing index for the first one of a plurality of chromatographic data pages generated correspondingly to the designed sample. By this processing, the analysis results of chromatographic data corresponding to the sample designated by the analyst can be displayed. By using the print previewing, the analyst confirms the contents of the analysis results of a plurality of unknown samples.

Figure 4:
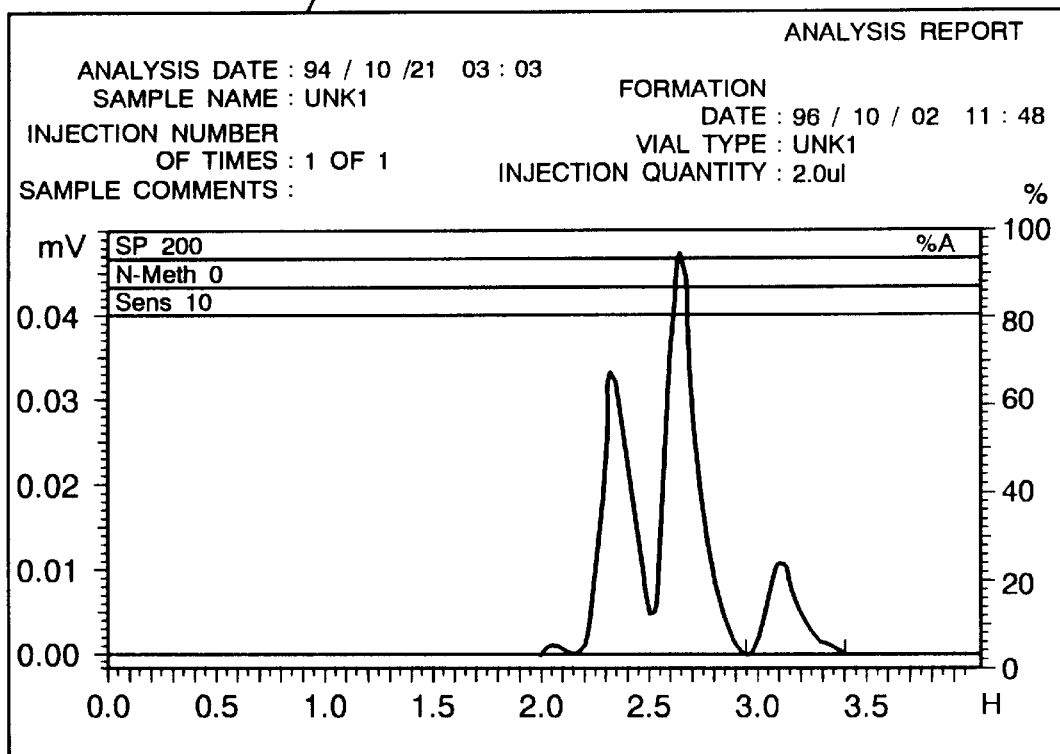
FIG. 4 is a view showing an example of a screen displayed on a display unit of then output device depicted in FIG. 3.

FIG. 4 shows an example in which the first page of an analysis report is displayed in the case where an unknown sample UNK1 of vial No. 6 is designated from the sample information table.

Step 109: When the confirmation of the contents of the analysis results of the unknown sample is completed, the analyst erases the print previewing screen.

Step 110: When the confirmation of the calculation results of the unknown sample teaches the quantitative calculation results expected in the step 108 and 109, the analysis of the series of steps 101 to 109 is terminated. In this case, the analyst prints the analysis results as a report.

When the quantitative calculation results are contrariwise different from the contents expected, the situation of the routine goes back to the step 105 and the analysis conditions, particularly the data processing conditions are changed so that only quantitative calculation is executed under new data processing conditions to thereby retry data processing. When the retrial of data processing is completed, the contents of the quantitative calculation results are confirmed again by using the print previewing.

The case where such quantitative calculation is retried will be described below.

Generally, in chromatographic measurement, known standard samples (STANDARD 2, 3, 4 and 5) are used so that a calibration curve is generated as a reference of measurement in advance.

Figure 5:
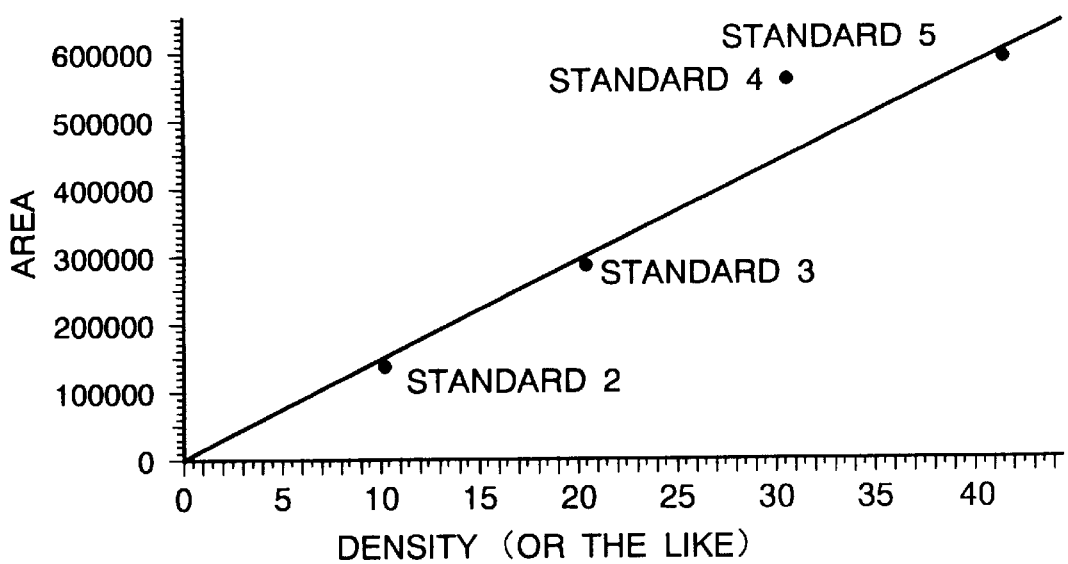
FIG. 5 is a graph showing an example of a calibration curve using standard samples in this embodiment.
Figure 6:
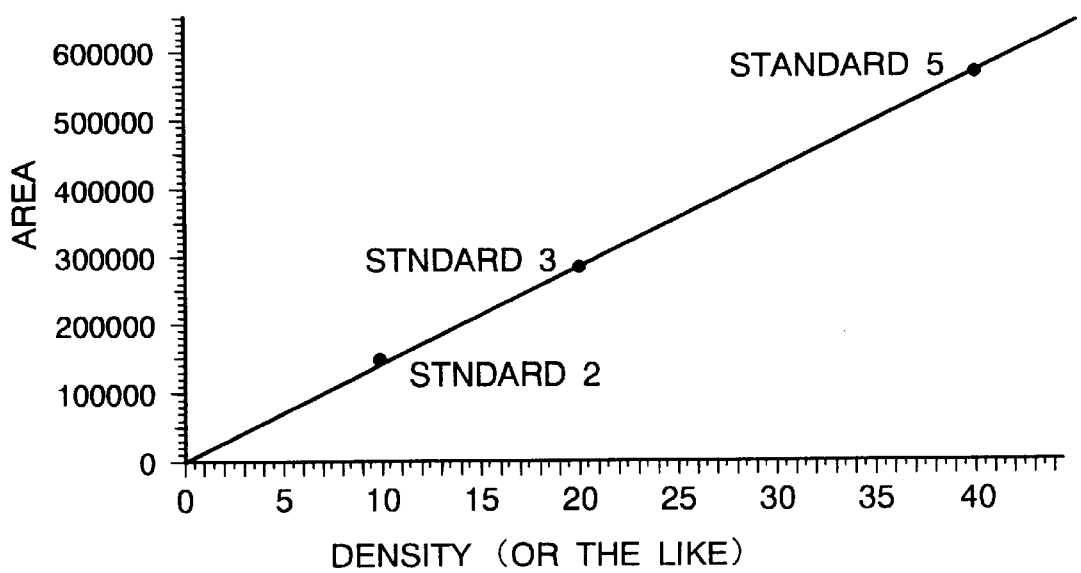
FIG. 6 is a graph showing an example of a calibration curve generated by using standard samples except unsuitable standard samples.

Assuming now that there is a data (STANDARD 4) out of the calibration curve because of occurrence of some failure, or the like, in the various devices of the chromatographic unit 311 as shown in FIG. 5. In this case, the calibration curve must be generated again from the three standard samples other than the standard sample (STANDARD 4).

In this case, standard samples STANDARD 2, 3 and 5 and unknown samples UNK1 to UNK4 are selected to retry calculation to thereby quantitatively measure the unknown samples UNK1 to UNK4 on the basis of a newly generated calibration curve.

FIG. 7 shows an information sample table portion thus obtained and a print preview constituted by the analysis report of the unknown sample UNK1.

Step 111: When the analyst judges that it is necessary to change the data processing conditions, the analysis results are sent to the printer.

As is obvious from the above description, the analyst can watch directly and speedily the analysis results corresponding to the unknown samples which the analyst requires because the page of the analysis results in print previewing is made to correspond to the sample information table in which the quantities of injected samples, the names of the samples and the vial numbers of the samples are arranged correspondingly to the injected samples. That is, print previewing of the analysis results can be performed directly and speedily.

In the aforementioned embodiment, it is possible to provide a liquid chromatograph suitable for performing print previewing of analysis results directly and speedily.

What is claimed is:

1. In a liquid chromatograph having a column, a device for pouring an eluting solution into said column to elute respective samples injected into said column to thereby separate components of said samples, a data processor for detecting and data processing said separated components to thereby obtain analysis results constituted by chromatograms and quantitative calculation results of said respective samples, and a display unit for displaying said analysis results, a method for processing liquid chromatographic data comprising the steps of:

storing said analysis results of said respective samples in a memory in said data processor with correspondence between the analysis results and said respective samples;

displaying, on said display unit, a sample information table expressing injection data concerning said samples injected;

reading said analysis results of a specific sample from said memory when the specific sample is designated from said sample information table; and displaying the read analysis results as a print preview on said display unit.

2. A method for processing liquid chromatographic data according to claim 1, wherein said sample table and said analysis results of said designated sample are displayed on one and the same screen.

3. A method for processing liquid chromatographic data according to claim 1, wherein when the analysis results in said print preview are judged to be unsuitable, data processing on the detected components is retried to thereby generate said analysis results.

4. A method for processing liquid chromatographic data according to claim 3, wherein in said retrial of data processing, reference data except unique data in standard samples are generated.

* * * * *